United States Patent [19]

Franklin

[11] Patent Number: 4,804,763

[45] Date of Patent: Feb. 14, 1989

[54] METHOD FOR PREPARING CHLORINE-CONTAINING DERIVATIVES OF PYRIDINE COMPOUNDS

[75] Inventor: James Franklin, Brussels, Belgium

[73] Assignee: Reilly Chemicals, S.A., Belgium

[21] Appl. No.: 767,771

[22] Filed: Aug. 19, 1985

[30] Foreign Application Priority Data

Aug. 20, 1984 [FR] France ................... 84 13049

[51] Int. Cl.$^4$ .................. C07D 213/61; C07C 17/00; C07C 21/18
[52] U.S. Cl. .................. 546/345; 570/181; 570/189
[58] Field of Search ............... 546/345; 570/181, 189

[56] References Cited

U.S. PATENT DOCUMENTS

| | | | |
|---|---|---|---|
| 2,516,402 | 7/1950 | McBee et al. | 546/345 |
| 3,173,919 | 3/1965 | Johnston et al. | 546/345 |
| 3,186,994 | 6/1965 | Johnston et al. | 546/345 |
| 3,418,323 | 12/1968 | Johnston et al. | 546/345 |
| 3,420,833 | 1/1969 | Johnston et al. | 546/345 |
| 3,424,754 | 1/1969 | Taplin | 546/345 |
| 4,205,175 | 5/1980 | Bowden et al. | 546/345 |
| 4,241,213 | 12/1980 | Nishiyama et al. | 546/345 |
| 4,256,894 | 3/1981 | Dietsche et al. | 546/345 |
| 4,257,857 | 3/1981 | Whittaker et al. | 546/345 |
| 4,259,496 | 3/1981 | Whittaker | 546/345 |
| 4,284,783 | 8/1981 | Whittaker et al. | 546/345 |
| 4,288,599 | 9/1981 | Nishiyama et al. | 546/345 |
| 4,288,600 | 9/1981 | Roberts et al. | 546/345 |
| 4,309,548 | 1/1982 | Wilson et al. | 546/345 |
| 4,317,913 | 3/1982 | Cartwright | 546/345 |
| 4,324,627 | 4/1982 | Cartwright | 546/345 |
| 4,331,811 | 5/1982 | Werner et al. | 546/345 |
| 4,393,214 | 7/1983 | Roberts et al. | 546/345 |
| 4,417,055 | 11/1983 | Nishiyama et al. | 546/345 |
| 4,420,618 | 12/1983 | Yokomichi et al. | 546/345 |
| 4,483,993 | 11/1984 | Marinak et al. | 546/345 |
| 4,487,935 | 12/1984 | Marinak et al. | 546/345 |
| 4,497,955 | 2/1985 | Marinak et al. | 546/345 |
| 4,508,907 | 4/1985 | Cartwright | 546/345 |
| 4,517,369 | 5/1985 | Marinak et al. | 546/345 |
| 4,555,575 | 11/1985 | Cartwright | 546/345 |
| 4,563,529 | 1/1986 | Nishiyama et al. | 546/345 |
| 4,563,531 | 1/1986 | Marinak et al. | 546/345 |
| 4,564,681 | 1/1986 | Marinak et al. | 546/345 |
| 4,577,027 | 3/1986 | Marinak et al. | 546/345 |
| 4,661,648 | 4/1987 | Franklin | 546/345 |

FOREIGN PATENT DOCUMENTS 0013474  11/1979  European Pat. Off. ............ 546/345

OTHER PUBLICATIONS

Chem. Abstracts, 68, No. 23 (1968), p. 10065, 104,400a.

Primary Examiner—Mary C. Lee
Assistant Examiner—Robert C. Whittenbaugh
Attorney, Agent, or Firm—Woodard, Emhardt, Naughton, Moriarty & McNett

[57] ABSTRACT

The reactions of chlorination of the pyridine compounds are conducted by means of molecular chlorine, with the use, as free-radical forming initiator, of a decachlorobutane or an octachlorobutene such as octachlorobutene-1 or a crude mixture of these chlorine-containing products obtained by additive chlorination of hexachlorobutadiene-1,3.

Good rates of conversion are obtained, and good yields at moderate temperatures.

The method is applied, for example, to the chlorination of pyridine and beta-picoline.

11 Claims, No Drawings

METHOD FOR PREPARING CHLORINE-CONTAINING DERIVATIVES OF PYRIDINE COMPOUNDS

The present invention relates to a method for preparing chlorine-containing derivatives of pyridine compounds such a 2-chloro pyridine and 2-chloro-5-trichloromethylpyridine from the corresponding pyridine compounds, by substitutive chlorination in the presence of initiators leading to free radicals.

To date, a variety of techniques have been developed for the preparation of chlorine-containing derivatives of pyridine compounds. One of these techniques consists more particularly in the preparation of 2-chloropyridine by a chlorination reaction of pyridine using molecular chlorine. This technique was the object of method developments that can be divided into two main classes.

A first class comprises the so-called thermal methods conducted in the vapor phase at high temperature, generally above 250° V. and even 300° to 400° C. and described in particular in U.S. Pats. Nos. 2,820,791 and 3,153,044 in the name of Olin Mathieson. These methods have various disadvantages such as a substantial formation of tars that produce clogging of the reactor or the pipes, and makes a continuous operation of the method difficult. Furthermore these methods are accompanied, according to the inventors, by serious risks of explosion and corrosion.

A second class of methods comprises the methods initiated by means of light or ultra-violet rays. Such methods have been described, for example, in U.S. Pats. Nos. 3,297,556 in the name of Olin Mathieson and 4,054,499 in the name of Seitetsu Kagaku Co. These methods, although they can be operated at temperatures lower than the so-called thermal ones, have the drawback of leading to the formation of tarry by-products that foul the light tubes and give rise to a subsequent reduction in the initiation radiation and hence in the efficiency of the reaction. Moreover, these methods necessitate operating in reactors permeable to the initiation radiation, that is to say, made of glass for the most part, and hence reactions conducted at high pressures are impracticable.

The present invention intends to remedy the drawbacks of the known methods while making it possible to make profitable use of an annoying by-product of certain productions of organic chlorine-containing products. As a matter of fact, the invention recommends conducting the substitutive chlorination of organic compounds by means of molecular chlorine in the presence of a new initiator that makes it possible to operate at moderate temperatures and in spite of all, obtain an excellent rate of chlorination. Moreover, the invention makes it possible to operate at pressures equal to or higher or lower than atmospheric pressure. The initiator consists of a chlorine-containing derivative of hexachlorobutadiene-1,3 which constitutes,—as we know— a toxic by-product with practically no uses, which up to now had to be destroyed by burning.

With this in mind, the invention relates to a method for the preparation of chlorine-containing derivatives of pyridine compounds by a reaction of substitutive chlorination of the corresponding pyridine compounds by means of molecular chlorine in the presence of a chlorine-containing product serving as a free-radical forming initiator in which the initiator utilized is a chlorine-containing product such as decachlorobutane or an octachlorobutene such as octachlorobutene-1 or a mixture containing these two products. Preferably, the chlorine-containing products or their mixtures involved in the method according to the invention are obtained by additive chlorination of hexachlorobutadiene-1,3.

The invention therefore also bears on the initiators of substitutive chlorination of the pyridine compounds consisting of a single chlorine-containing product or a mixture of chlorine-containing products that results from the additive chlorination of hexachlorobutadiene-1,3 and which comprises, primarily, decachlorobutane and/or an octachlorobutene such as octachlorobutene-1 depending on the degree to which the additive chlorination was pushed.

The said chlorine-containing products obtained by additive chlorination of hexachlorobutadeiene-1,3 can be prepared in known fashion, for example by photochlorination or by chlorination in liquid phase catalyzed by iron.

These chlorinations lead to the formation of crude mixtures which contain, in addition to the main products mentioned above, a little hexachlorethane and perhaps untransformed hexachlorobutadiene-1,3, as well as a small proportion of other compounds.

Thus, by way of example, we present below the composition of crude mixtures resulting from the photochlorination of hexachlorobutadiene-1,3 at 3° C., in g/kg:

|  | Mixture A | Mixture B |
|---|---|---|
| Octachlorobutene-1 | 415 | — |
| Decachlorobutane | 303 | 812 |
| Hexachloroethane | 183 | 147 |
| Hexachlorobutadiene-1,3 | 77 | <0.5 |
| Other unidentified compounds | 22 | 41 |

Furthermore, a crude mixture obtained by chlorination of hexachlorobutadiene-1,3 (1190 g of $C_4Cl_6$ and 652 g of $Cl_2$) in the autoclave, at 125° C., and a press bars, in the presence of about 0.1% by weight of $FeCl_3$ (catalyst), the product of chlorination having been washed in hydrochloric acid to eliminate the $DeCl_3$, had the following composition:

|  | Mixture C, g/kg |
|---|---|
| Octachlorobutene-1 | 200 |
| Decachlorobutane | 615 |
| Hexachloroethane | 128 |
| Hexachlorobutadiene-1,3 | 25 |
| Other unidentified compounds | 32 |

The quantity of initiator involved in the method of the invention is comprised in general between 0.01 and 10 moles % of the total quantity of reagents and diluents used. This quantity is generally 0.01 to 5 moles % and it is preferable to work with 0.1 to 2 moles % of initiator relative to the reagents involved.

The molecular chlorine and the pyridine compounds are usually involved in molar ratios comprised between 0.1 and 20 moles of chlorine per mole of pyridine compound. This ratio depends in particular on the number of hydrogen atoms that are to be substituted. Preferably this ratio ranges between 0.2 and 15 moles and very special preference goes to molar ratios situated between 0.3 and 10 moles of chlorine per mole of pyridine. When 2-chloropyridine is to be made from pyridine, the preferred molar ratio lies between 0.2 and 2 moles of chlorine per mole of pyridine. When making 2-chloro-5-trichloromethyl pyridine the preferred ratio lies between 2 and 20 moles of chlorine per mole of 3-methylpyridine (beta-picoline) involved.

The chlorination initiators mentioned above are suitable for reactions in gas phase or liquid phase. They can be used at atmospheric pressure or at a higher pressure. The reaction temperature depends of course on the nature of the compound to be chlorinated and on the other operating conditions, but in any event with a given rate of chlorination and time of stay, the use of the initiators according to the invention permits reducing the temperature and improving the selectivity, and reducing the formation of tars and the appearance of fouling observed at high temperature;

at a given temperature and time of stay, it is possible to attain a higher chlorination rate, which can lead to a saving of energy by reduction of the quantity of pyridine compounds to be recycled;

at a given temperature and chlorination rate, it is possible to reduce the time of stay, which means an increase in productivity of the reactor.

Aside from the reagents and initiators already cited, it is advantageously possible to make use, in the method according to the invention, of additives such as water vapor, nitrogen and/or other gases not participating in the chlorination reaction properly speaking. As a rule the chlorination reaction is conducted in the presence of water vapor at the rate of 0.1 to 25 moles per mole of pyridine compound involved. It is preferable to use water vapor quantities of 1 to 15 moles per mole of pyridine compound. The addition of these additives, and more especially of water vapor, can be embodied in any way at all. One advantageous way consists in premixing the water and the pyridine compound, sending this mixture into an evaporator and then injecting the vapors thus obtained into the chlorination reactor properly speaking.

It has also been found desirable in certain cases, in order to minimize the superheating of the reaction mixture and avoid the condensation of the little-volatile reaction products, to conduct the chlorination reaction in the presence of additives acting as diluents, but inert with respect to the reagents and initiators intervening in the chlorination reaction. It is preferable to use, as additives, chlorine-containing derivatives of aliphatic compounds such as carbon tetrachloride or inorganic products such as hydrogen chloride or nitrogen.

It is preferable to operate with carbon tetrachloride.

In general, the halogenated organic additives are added to the reaction medium at the rate of 1 to 25 moles per mole of pyridine compound involved. When carbon tetrachloride is used as organic additive, the preferred quantities lie between 1.5 and 15 moles per mole of pyridine compound involved.

The method according to the invention can be embodied in any apparatus or any reactor in which the operating conditions described above can be combined. Good results have been obtained in the apparatus described in the examples below.

The chlorine-containing derivatives of the pyridine compounds obtained according to the method of the invention can be used in every known application of this product, that is to say as a chemical intermediary in the manufacture, for example, of products used in agriculture, cosmetics and pharmaceutical products.

The examples which follow will serve to illustrate the invention without, however, limiting the scope thereof.

EXAMPLE 1

In this example the substitutive chlorination of pyridine was carried out at 230° C. in order to obtain 2-chloropyridine.

The chlorination of pyridine in the gas phase was carried out at atmospheric pressure in a spherical, continuous mixing reactor of about 1 dm$^3$, made of pyrex and self agitated by gas jets (Chem. Eng Sci., 1973, 28, p. 129–137), the reagents being introduced in gas form with the aid of a four-nozzle injector placed in the center of the sphere.

The reactor is placed in an enclosure inside which the air is heated electrically and agitated with the aid of a turbine, in order to maintain the desired reaction temperature. The pyridine-water mixture is fed through a vertical tubular evaporator, heated by electricity. The diluent ($CCl_4$), used to moderate the thermal effect of the reaction is fed through a second, identical evaporator. The gaseous chlorine is injected at the foot of the $CCl_4$ evaporator. The initiator, when used, is added in liquid form in solution in $CCl_4$, through a branch opening into the duct feeding the gas mixture of $CCl_4 + Cl_2$. The products of chlorination emerge from the reactor through a tube diametrically opposite the input, then they are condensed, treated with aqueous NaOH to neutralize the residual chlorine and the HCl formed. After decantation the organic phase is separated from the aqueous phase; the latter is subjected to an extraction with chloroform and the organic phase as well as the chloroform extract are analyzed by chromatography in vapor phase. The total nitrogen in the aqueous phase extracted is determined by the Kjeldahl method. The conditions and the results of the tests are given in table 1 below.

TABLE 1

|  |  | Reference test without initiator | Test with initiator (mixture C) |
|---|---|---|---|
| Conditions |  |  |  |
| temperature in reactor | °C. | 230 | 229 |
| temperature, evaporator I outlet ($CCl_4 + Cl_2$) | °C. | 164 | 163 |
| temperature, evaporator II outlet (pyridine + $H_2O$) | °C. | 182 | 188 |
| introduction of initiator |  | none | solution, 56% by weight in $CCl_4$ |
| average time of stay* | S | 10 | 10 |
| molar ratios of reagent |  |  |  |
| pyridine | mol/mol | 1 | 1 |
| $Cl_2$ | mol/mol | 0.67 | 0.68 |
| $CCl_4$ (inert diluent) | mol/mol | 2.4 | 2.4 |
| $H_2O$ (inert diluent) | mol/mol | 1.1 | 1.1 |
| initiator (sum of constituents) | mol/mol | 0 | 0.06 |
| initiator content of reaction mixture | % mol | 0 | 1.1 |
| Results |  |  |  |
| distribution of chlorination products |  |  |  |
| pyridine | % mol | 86.2 | 52.0 |
| 2-chloropyridine | % mol | 7.2 | 42.6 |
| 3- and 4-chloropyridines | % mol | 0.1 | 0.3 |
| 2,6-dichloropyridines | % mol | 0.1 | 4.3 |
| other dichloropyridines | % mol | <0.1 | 0.8 |
| nitrogenous compounds, not extractable (by $CHCl_3$) in the aqueous phase | % mol | 6.3 | <0.1 |
| 2-chloropyridine formed/$Cl_2$ involved | mol/mol | 0.11 | 0.63 |
| rate of chlorination 1 | mol/mol | 0.08 | 0.53 |

TABLE 1-continued

|  |  | Reference test without initiator | Test with initiator (mixture C) |
|---|---|---|---|
| (moles of Cl fixed on pyridine/moles of pyridine involved) |  |  |  |
| rate of chlorination 2 (moles of Cl fixed on pyridine/moles of Cl$_2$ involved) | mol/mol | 0.11 | 0.78 |

*time of stay = $\dfrac{\text{volume of reactor}}{\text{voluminal flow of reagents at reaction temperature}}$ This table shows that in the absence of an initiator, at 230° C., only a low conversion of pyridine into 2-chloropyridine is observed; a quantity of water-soluble by-products (not extractable in chloroform) is formed, which is almost as large as the quantity of 2-chloropyridine produced.

The addition of 1.1% mol/sic/ of the product of additive chlorination of hexachlorobutadiene-1,3 permits a very substantial increase in the advancement of the reaction:
- the ratio of 2-chloropyridine formed/Cl$_2$ involved changes from 0.11 to 0.63 mol/mol;
- the ratio of Cl fixed on pyridine/pyridine involved changes from 0.08 to 0.53 mol/mol/
- the ratio of Cl fixed on pyridine/Cl$_2$ involved changes from 0.11 to 0.78 mol/mol.

EXAMPLE 2

The substitutive chlorination of beta-picoline was operated in order to obtain 2-chloro-5-trichloromethylpyridine. The installation and the method used were identical to those in example 1. The conditions and results of the test are given in table 2 below.

It is evident here that in the absence of initiator, at about 300° C., a certain chlorination of the beta-picoline does take place, but the yield of 2-chloro-5-trichloromethylpyridine is low (about 2% of the beta-picoline involved), the principal products being mono-, di- and tri-chlorinated beta-picolines.

The addition of 0.3% mol of the product of additive chlorination of hexachlorobutadiene-1,3 makes it possible to bring the yield of 2-chloro-5-trichloromethylpyridine from 2 to 27% relative to the beta-picoline involved. The rate of chlorination (moles of Cl fixed on the beta-picoline/moles (of beta-picoline involved) changes from 1.70 to 3.22 mol/mol. The proportion of beta-picoline transformed into watersoluble by-products (not extractable in chloroform) diminishes from 6.1 to <0.6% of the beta-picoline involved.

TABLE 2

|  |  | Reference test without initiator | Test with initiator (mixture C) |
|---|---|---|---|
| Conditions |  |  |  |
| temperature in reactor | °C. | 301 | 303 |
| temperature, evaporator I outlet (CCl$_4$ + Cl$_2$) | °C. | 136 | 137 |
| temperature, evaporator II outlet (β-picoline + H$_2$O) | °C. | 185 | 192 |
| introduction of initiator |  | none | solution, 11% by weight in CCl$_4$ |
| average time of stay | s | 10 | 10 |
| molar ratios of reagents |  |  |  |
| β-picoline | mol/mol | 1 | 1 |
| Cl$_2$ | mol/mol | 6.3 | 6.8 |
| CCl$_4$ (inert diluent) | mol/mol | 11 | 11 |
| H$_2$O (inert diluent) | mol/mol | 1.1 | 1.1 |
| initiator (sum of constituents) | mol/mol | 0 | 0.06 |
| initiator content of of reaction mixture | % mol | 0 | 0.30 |
| Results |  |  |  |
| distribution of chlorination products |  |  |  |
| β-picoline | % mol | 15.2 | 0.9 |
| monochloro-β-picolines | % mol | 20.7 | 2.9 |
| dichloro-β-picolines | % mol | 29.3 | 11.6 |
| trichloro-β-picolines | % mol | 24.2 | 43.7 |
| 2-chloro-5-trichloromethylpyridine | % mol | 2.1 | 26.5 |
| 2-chloro-3-trichloromethylpyridine | % mol | 0.6 | 8.8 |
| other tetrachloro-β-picolines | % mol | 1.8 | 1.9 |
| 2,6-dichloro-3-trichloromethylpyridine | % mol | <0.1 | 3.2 |
| nitrogenous compounds not extractable in the aqueous phase | % mol | 6.1 | <0.6 |
| 2-chloro-5-trichloro methylpyridine formed β-picoline involved | mol/mol | 0.02 | 0.27 |
| rate of chlorination (moles of Cl fixed on β-picoline/moles of β-picoline involved) | mol/mol | 1.70 | 3.22 |

I claim:

1. Method for preparing chlorine-containing derivatives of pyridine compounds by a reaction of substitutive chlorination of the corresponding pyridine compounds by means of molecular chlorine in the presence of a chlorine-containing product serving as an initiator forming free radicals, characterized in that the initiator consists of a chlorine-containing product such as decachlorobutane or an octachlorobutene such as octachlorobutene-1, or a mixture containing these two products.

2. Method according to claim 1, characterized in that the initiator involved results from the additive chlorination of hexachlorobutadiene-1,3.

3. Method according to claims 1 or 2, characterized by the use of the initiator in a quantity comprised between 0.1 and 5 mole % relative to the reagents and diluents involved.

4. Method according to claims 1 or 2, characterized in that we operate at a pressure higher than atmospheric pressure.

5. Method according to claims 1 or 2, characterized in that it is applied to the substitutive chlorination of pyridine into 2-chloropyridine.

6. Method according to claims 1 or 2, characterized in that it is applied to the substitutive chlorination of beta-picoline into 2-chloro-5-trichloromethylpyridine.

7. The method of claim 3, characterized in that we operate at a pressure higher than atmospheric pressure.

8. The method according to 3, characterized in that it is applied to the substitutive chlorination of pyridine into 2-chloropyridine.

9. The method according to 3, characterized in that it is applied to the substitutive chlorination of pyridine into 2-chloropyridine.

10. The method according to claim 3, characterized in that it is applied to the substitutive chlorination of beta-picoline into 2-chloro-5-trichloromethylpyridine.

11. The method according to claim 4, characterized in that it is applied to the substitutive chlorination of beta-picoline into 2-chloro-5-trichloromethylpyridine.

* * * * *

UNITED STATES PATENT AND TRADEMARK OFFICE
CERTIFICATE OF CORRECTION

PATENT NO. : 4,804,763
DATED : February 14, 1989
INVENTOR(S) : James Franklin

It is certified that error appears in the above-identified patent and that said Letters Patent is hereby corrected as shown below:

In TABLE 1, column 4, lines 36-69, and continued at column 5, lines 1-13, cancel the entire contents of such TABLE 1, and insert in lieu thereof the following replacement table as shown on pages 1 and 2:

TABLE 1

|  |  | Reference test without initiator | Test with initiator (mixture C) |
|---|---|---|---|
| Conditions | | | |
| - temperature in reactor | °C | 230 | 229 |
| - temperature, evaporator I outlet ($CCl_4$ + $Cl_2$) | °C | 164 | 163 |
| - temperature, evaporator II outlet (pyridine + $H_2O$) | °C | 182 | 188 |
| - introduction of initator | | none | solution, 56% by weight in $CCl_4$ |
| - average time of stay* | s | 10 | 10 |
| - molar ratios of reagents | | | |
| • pyridine | mol/mol | 1 | 1 |
| • $Cl_2$ | mol/mol | 0.67 | 0.68 |
| • $CCl_4$ (inert diluent) | mol/mol | 2.4 | 2.4 |
| • $H_2O$ (inert diluent) | mol/mol | 1.1 | 1.1 |
| • initiator (sum of constituents) | mol/mol | 0 | 0.06 |

UNITED STATES PATENT AND TRADEMARK OFFICE
CERTIFICATE OF CORRECTION

PATENT NO. : 4,804,763
DATED : February 14, 1989
INVENTOR(S) : James Franklin

It is certified that error appears in the above-identified patent and that said Letters Patent is hereby corrected as shown below:

| | | | |
|---|---|---|---|
| - initiator content of of reaction mixture | % mol | 0 | 1.1 |
| Results | | | |
| - distribution of chlorination products | | | |
| • pyridine | % mol | 86.2 | 52.0 |
| • 2-chloropyridine | % mol | 7.2 | 42.6 |
| • 3- and 4-chloropyridines | % mol | 0.1 | 0.3 |
| • 2,6-dichloropyridines | % mol | 0.1 | 4.3 |
| • other dichloropyridines | % mol | < 0.1 | 0.8 |
| • nitrogenous compounds, not extractable (by $CHCl_3$) in the aqueous phase | % mol | 6.3 | < 0.1 |
| - 2-chloropyridine formed/$Cl_2$ involved | mol/mol | 0.11 | 0.63 |
| - rate of chlorination 1 (moles of Cl fixed on pyridine/moles of pyridine involved) | mol/mol | 0.08 | 0.53 |
| - rate of chlorination 2 (moles of Cl fixed on pyridine/moles of $Cl_2$ involved) | mol/mol | 0.11 | 0.78 |

*time of stay = $\dfrac{\text{volume of reactor}}{\text{voluminal flow of reagents at reaction temperature}}$

UNITED STATES PATENT AND TRADEMARK OFFICE
CERTIFICATE OF CORRECTION

PATENT NO. : 4,804,763

DATED : February 14, 1989

INVENTOR(S) : James Franklin

It is certified that error appears in the above-identified patent and that said Letters Patent is hereby corrected as shown below:

In TABLE 2, column 5, lines 53-68, and continued at column 6, lines 1-28, cancel the entire contents of such TABLE 2, and insert in lieu thereof the following replacement table shown on pages 3 through 5:

TABLE 2

|  |  | Reference test without initiator | Test with initiator (mixture C) |
|---|---|---|---|
| Conditions | | | |
| - temperature in reactor | °C | 301 | 303 |
| - temperature, evaporator I outlet ($CCl_4 + Cl_2$) | °C | 136 | 137 |
| - temperature, evaporator II outlet (ß-picoline + $H_2O$) | °C | 185 | 192 |
| - introduction of initator | | none | solution, 11% by weight in $CCl_4$ |
| - average time of stay | s | 10 | 10 |
| - molar ratios of reagents | | | |
| • ß-picoline | mol/mol | 1 | 1 |
| • $Cl_2$ | mol/mol | 6.3 | 6.8 |
| • $CCl_4$ (inert diluent) | mol/mol | 11 | 11 |

UNITED STATES PATENT AND TRADEMARK OFFICE
CERTIFICATE OF CORRECTION

PATENT NO. : 4,804,763

DATED : February 14, 1989

INVENTOR(S) : James Franklin

It is certified that error appears in the above-identified patent and that said Letters Patent is hereby corrected as shown below:

|  |  |  |  |
|---|---|---|---|
| • $H_2O$ (inert diluent) | mol/mol | 1.1 | 1.1 |
| • initiator (sum of constituents) | mol/mol | 0 | 0.06 |
| - initiator content of of reaction mixture | % mol | 0 | 0.30 |
| Results |  |  |  |
| - distribution of chlorination products |  |  |  |
| • ß-picoline | % mol | 15.2 | 0.9 |
| • monochloro-ß-picolines | % mol | 20.7 | 2.9 |
| • dichloro-ß-picolines | % mol | 29.3 | 11.6 |
| • trichloro-ß-picolines | % mol | 24.2 | 43.7 |
| • 2-chloro-5-trichloro-methylpyridine | % mol | 2.1 | 26.5 |
| • 2-chloro-3-trichloro-methylpyridine | % mol | 0.6 | 8.8 |
| • other tetrachloro-ß-picolines | % mol | 1.8 | 1.9 |
| • 2,6-dichloro-3-trichloromethylpyridine | % mol | < 0.1 | 3.2 |
| • nitrogenous compounds not extractable in the aqueous phase | % mol | 6.1 | < 0.6 |

UNITED STATES PATENT AND TRADEMARK OFFICE
CERTIFICATE OF CORRECTION

PATENT NO. : 4,804,763
DATED : February 14, 1989
INVENTOR(S) : James Franklin

It is certified that error appears in the above-identified patent and that said Letters Patent is hereby corrected as shown below:

| | | | |
|---|---|---|---|
| - 2-chloro-5-trichloro-methylpyridine formed β-picoline involved | mol/mol | 0.02 | 0.27 |
| - rate of chlorination (moles of Cl fixed on β-picoline/moles of β-picoline involved) | mol/mol | 1.70 | 3.22 |

Signed and Sealed this

Seventeenth Day of April, 1990

Attest:

HARRY F. MANBECK, JR.

Attesting Officer

Commissioner of Patents and Trademarks